(12) United States Patent
Blackwell et al.

(10) Patent No.: US 8,486,346 B2
(45) Date of Patent: Jul. 16, 2013

(54) GAS SCRUBBER FOR AUTOMATED CLINICAL ANALYZER

(75) Inventors: Gregory A. Blackwell, Dallas, TX (US); Patrick P. Fritchie, Southlake, TX (US); Ganesh Rajagopal, Carrollton, TX (US); James W. Whitt, Valley View, TX (US)

(73) Assignee: Abbott Laboratories, Abbott Park, IL (US)

( * ) Notice: Subject to any disclaimer, the term of this patent is extended or adjusted under 35 U.S.C. 154(b) by 1334 days.

(21) Appl. No.: 12/122,928

(22) Filed: May 19, 2008

(65) Prior Publication Data

US 2009/0282932 A1 Nov. 19, 2009

(51) Int. Cl.
*G01N 15/06* (2006.01)
*G01N 33/00* (2006.01)
*G01N 33/48* (2006.01)

(52) U.S. Cl.
USPC ............ 422/408; 422/50; 422/401; 422/402; 422/416; 422/417; 422/62; 422/63; 422/68.1; 422/88; 436/43; 436/63; 436/64; 436/501; 436/175; 436/178

(58) Field of Classification Search
USPC ............... 422/50, 401, 62, 63, 68.1, 88, 402, 422/408, 416, 417; 436/43, 63, 64, 501, 175, 436/178
See application file for complete search history.

(56) References Cited

U.S. PATENT DOCUMENTS

| 3,824,167 | A | * | 7/1974 | Oswin et al. ............... 204/411 |
| 3,892,549 | A | | 7/1975 | Lyshkow |
| 5,610,073 | A | | 3/1997 | Chu et al. |

(Continued)

FOREIGN PATENT DOCUMENTS

| EP | 0731355 A2 | 9/1996 |
| EP | 0766087 B1 | 4/1997 |

(Continued)

OTHER PUBLICATIONS

Abbott Diagnostics Division, ARCHITECT® System ESTRADIOL, package insert, REF 7K72, B7K720, 77-3692/R2 (Nov. 2006), pp. 1-8.

(Continued)

*Primary Examiner* — Brian J Sines
(74) *Attorney, Agent, or Firm* — Hanley, Flight & Zimmerman, LLC (57) ABSTRACT

A device and method for extending the useful life of a bulk liquid used in an automated clinical analyzer. Air from the atmosphere surrounding the automated clinical analyzer that displaces the bulk liquid consumed from a container is routed through a gas scrubber in order to remove or at least reduce the quantity of at least one contaminant present in that air. The gas scrubber is positioned between the bulk liquid in the container and the atmosphere surrounding the container. The gas scrubber contains a reagent that is capable of reacting with a contaminant in the atmosphere, whereby a required characteristic(s) of the bulk liquid does (do) not change excessively prior to the date that the bulk liquid is consumed. For example, if the contaminant is carbon dioxide, and the required characteristic of the bulk liquid is the level of pH of the bulk liquid, the reagent in the gas scrubber prevents the level of pH of the bulk liquid from changing excessively prior to the date that the bulk liquid is consumed.

20 Claims, 3 Drawing Sheets

U.S. PATENT DOCUMENTS

| | | | |
|---|---|---|---|
| 5,795,784 A | 8/1998 | Arnquist et al. | |
| 5,856,194 A | 1/1999 | Arnquist et al. | |
| 6,127,140 A | 10/2000 | Vidakovic et al. | |
| 6,218,174 B1 | 4/2001 | Keyser | |
| 7,329,307 B2 | 2/2008 | Hrycak et al. | |
| 7,846,739 B2* | 12/2010 | von Bahr et al. | 436/116 |
| 8,449,839 | 5/2013 | Rajagopal et al. | |
| 2003/0208133 A1* | 11/2003 | Mault | 600/532 |
| 2003/0223472 A1 | 12/2003 | Ravalico et al. | |
| 2004/0082872 A1* | 4/2004 | von Bahr et al. | 600/532 |
| 2005/0160913 A1 | 7/2005 | Hrycak et al. | |
| 2005/0279387 A1 | 12/2005 | Blackwell et al. | |
| 2006/0118167 A1 | 6/2006 | Neas et al. | |
| 2006/0263248 A1 | 11/2006 | Gomm et al. | |
| 2008/0154543 A1 | 6/2008 | Rajagopal et al. | |
| 2011/0066060 A1* | 3/2011 | von Bahr et al. | 600/532 |

FOREIGN PATENT DOCUMENTS

| | | |
|---|---|---|
| GB | 2083622 A | 3/1982 |
| JP | 8304407 A | 11/1996 |
| JP | 2000009734 A | 1/2000 |
| JP | 2000214171 A | 8/2000 |
| WO | WO97/12677 A | 4/1997 |
| WO | 0128701 A1 | 4/2001 |
| WO | 03062796 A1 | 7/2003 |
| WO | 2004076034 A1 | 9/2004 |

OTHER PUBLICATIONS

Fitting for Fluid Systems 135. Class information [online]. Toolingu, Tooling University, LLC., Hydraulics and Pneumatics Department, 2008 [retrieved on Nov. 14, 2008]. <URL: http://www.toolingu.com/class-570135-fittings-for-fluid-systems.html>.

Automated analyser. Encyclopedia [online]. Wikipedia [retrieved on May 13, 2008]. Retrieved from the Internet: <URL: http://en.wikipedia.org/wiki/Automated_analyser>.

Check valve. Encyclopedia [online]. Wikipedia [retrieved on May 19, 2008]. Retrieved from the Internet: <URL: http://en.wikipedia.org/wiki/Check_valve>.

Level sensor. Encyclopedia [online]. Wikipedia [retrieved on May 13, 2008]. Retrieved from the Internet: <URL: http://en.wikipedia.org/wiki/Level_sensor>.

Scrubber. Encyclopedia [online]. Wikipedia [retrieved on Mar. 7, 2008]. Retrieved from the Internet: <URL: http://en.wikipedia.org/wiki/Scrubber>.

PCT International Search Report, Sep. 3, 2009.

English Translation of Office Action, issued by the Japanese Patent Office in connection with Patent Application No. 2011-510612, on Jan. 22, 2013, 5 pages.

* cited by examiner

GAS SCRUBBER FOR AUTOMATED CLINICAL ANALYZER

BACKGROUND OF THE INVENTION

1. Field of the Invention

This invention relates to treatment of contaminants in the environment so that they do not contaminate the liquid in a container, more particularly, a liquid to be used in an assay in an automated clinical analyzer.

2. Discussion of the Art

The members of the ARCHITECT® family of automated diagnostic analyzers, commercially available from Abbott Laboratories, require fluid handling systems that employ at least one sub-system for aspirating and dispensing samples and reagents, at least one sub-system for dispensing buffers, at least one sub-system for dispensing pre-trigger fluids and trigger fluids, and at least one sub-system for handling liquid waste.

Through aspiration processes, samples are moved from sample containers and assay reagents are moved from reagent containers for dispensing into reaction vessels. In addition, wash buffer is dispensed for priming and flushing. Trigger solutions and pre-trigger solutions are also dispensed into reaction vessels. Trigger solutions and pre-trigger solutions are normally stored on-board the automated diagnostic analyzers as bulk liquids in relatively large containers.

Bulk liquids are typically aspirated from containers, such as, for example, bottles, and the volume of liquid aspirated is displaced by air from the atmosphere surrounding the automated diagnostic analyzer, through a vent in a straw assembly. As a result, carbon dioxide, i.e., $CO_2$, from the atmosphere surrounding the automated diagnostic analyzer is absorbed by and dissolved in the bulk liquid, and the pH of the bulk liquid, namely the trigger solution, is lowered. The stability of the trigger solution when stored upon the automated diagnostic analyzer is approximately two weeks. After two weeks, the amount of carbon dioxide absorbed by and dissolved in the trigger solution lowers the pH of the trigger solution to a level that results in adversely affecting results of an assay.

EP 0 766 087 discloses a method for the detection of creatinine in which an aqueous solution containing creatinine is contacted with a dry reagent system containing an indicator for creatinine at a pH above about 11.5. The high pH is provided by a dry alkaline material upon its being hydrated by the aqueous fluid. The dry reagent is packaged with a material capable of absorbing carbon dioxide and at least some ambient water vapor. The carbon dioxide-absorbing material is provided in an amount sufficient to substantially inhibit the formation of carbonic acid in the area of the reagent system. This inhibition of the production of carbonic acid increases the shelf life of the creatinine-detecting device by reducing or eliminating the neutralization of the alkali reagent by carbonic acid formed in situ.

U.S. Pat. No. 6,218,174 discloses degassing by driving a gas-containing solution to sub-atmospheric pressure approximately equal to the solution vapor pressure, and maintaining the subatomic pressure not withstanding evolution of gas from the solution. This method may be accomplished using a vacuum tower arrangement whereby a column of gas-containing liquid is drawn to the maximum physically attainable height. So long as the vacuum is coupled to the liquid column above this height (generally on the order of 34 feet, depending on the ambient temperature and the composition of the liquid), the liquid will not be drawn into the vacuum, which creates a non-equilibrium region of extremely low pressure above the liquid that liberates dissolved gases.

U.S. Pat. No. 7,329,307 discloses a carbon dioxide removal system including a member having a first opening and a second opening to enable air flow and containing lithium hydroxide (LiOH) supported by the member and having an initial water content above an anhydrous level. U.S. Pat. No. 7,329,307 further discloses removal of carbon dioxide by including pre-hydrated LiOH adsorbent in a location having air flow with carbon dioxide. The carbon dioxide is removed with pre-hydrated LiOH adsorbent.

Accordingly, it is desired that the useful life of the trigger solution be extended as much as possible, so that the entire contents of the container of the trigger solution can be consumed prior to the date by which it has deteriorated excessively. It is further desired that the trigger solution have a useful life of at least about two weeks, and preferably longer, after being exposed to air in the atmosphere surrounding the automated diagnostic analyzer. It is still further desired that the pH of the trigger solution be maintained at the appropriate level for an extended period of time.

SUMMARY OF THE INVENTION

This invention provides a device and method for extending the useful life of a bulk liquid used in an automated clinical analyzer. Air from the atmosphere surrounding the automated clinical analyzer that displaces the bulk liquid consumed from a container is routed through a gas scrubber in order to remove or at least reduce the quantity of at least one contaminant present in that air. The gas scrubber is positioned between the bulk liquid in the container and the atmosphere surrounding the container. The container has a straw assembly, which straw assembly is connected to the outlet of the gas scrubber, preferably by a fluid line. The inlet of the gas scrubber can be connected to a fluid line that allows carbon dioxide from the atmosphere surrounding the automated clinical analyzer to enter the gas scrubber. However, the inlet of the gas scrubber can directly communicate with the atmosphere surrounding the automated clinical analyzer, thereby dispensing with the fluid line. The gas scrubber contains a reagent that is capable of reacting with a contaminant in the atmosphere, whereby a required characteristic(s) of the bulk liquid does (do) not change excessively prior to the date that the bulk liquid is consumed. For example, if the contaminant is carbon dioxide, and the required characteristic of the bulk liquid is the level of pH of the bulk liquid, the reagent in the gas scrubber prevents the level of pH of the bulk liquid from changing excessively prior to the date that the bulk liquid is consumed.

The gas scrubber described herein greatly reduces the quantity of gas absorbed by the bulk liquid and inhibits the lowering of the pH level of the bulk liquid. The useful life of the bulk liquid can be substantially extended by inhibiting the lowering of the pH value thereof. The effect of contamination by the atmosphere surrounding the automated clinical analyzer on the bulk liquid and the adverse effect on assay results on account of the deterioration of the bulk liquid can be substantially reduced.

BRIEF DESCRIPTION OF THE DRAWINGS

FIG. 3 also shows where the gas scrubber described herein can be positioned.

DETAILED DESCRIPTION

As used herein, the expression "automated clinical analyzer" means a medical laboratory instrument designed to measure different chemicals and other characteristics in a number of biological samples quickly, with minimal human assistance. These measured properties of blood and other fluids may be useful in the diagnosis of disease. Automated clinical analyzers include, but are not limited to, routine biochemistry analyzers, immuno-based analyzers, and hematology analyzers, such as, for example, cell counters, coagulometers. As used herein, the expression "automated diagnostic analyzer" means a diagnostic analyzer wherein involvement of an operator in the assay processing steps is minimal. As used herein, the expression, "on-board container" means a container that fits within the confines of the automated clinical analyzer and is capable of moving with the analyzer when the analyzer is moved.

As used herein, the term "fluid" means a substance, such as, for example, a liquid or a gas, that exists as a continuum marked by low resistance to flow and the tendency to assume the shape of its container. The fluids of primary concern with respect to the invention described herein are the trigger solution, the pre-trigger solution, and air. However, the term "fluid" also includes any fluid that is adversely affected by a contaminant that can be treated by a gas scrubber of the type described herein.

As used herein, the expression "displacement air" means air from the environment external to a system that displaces bulk liquid from a container of bulk liquid when the bulk liquid is consumed during operation of the system. For example, when a quantity of trigger solution is withdrawn from a container to be used in the system, displacement air external to the system replaces the quantity of trigger solution withdrawn. As used herein, the expression "straw assembly" means an assembly of components in which a slender tube is used in order to suck up a liquid. As used herein, the expression "pick-up device" means device that comprises the straw assembly. As used herein, the expression "bulk liquid" means liquid that is provided in a container for a relatively large number of chemical reactions. For example, a trigger solution can be supplied as a bulk liquid in a large container, wherein the container of trigger solution is expected to be used for approximately 3,000 tests. In general, a typical immunoassay for an ARCHITECT® automated immunoassay analyzer consumes approximately 300 microliters of the bulk liquid. Because a low volume diagnostic laboratory rarely carries out 3,000 tests within a two-week period, the trigger solution supplied to a low-volume diagnostic laboratory is likely to deteriorate prior to its being completely consumed.

As used herein, the term "immunoassay" means a biochemical test that measures the concentration of a substance in a biological liquid, typically serum, using the reaction of an antibody (antibodies) to its (their) antigen. An immunoassay takes advantage of the specific binding of an antibody to its antigen. As used herein, a "chemiluminescent microparticle immunoassay", alternatively referred to as "chemiluminescent magnetic immunoassay", involves a chemiluminescent label conjugated to the antibody or the antigen. In one type of this assay, a magnetic microparticle is coated with antibodies. The assay is intended to look for antigens in the sample. A second antibody is labeled with a chemiluminescent label. This second antibody is not attached to a magnetic microparticle. The antibody and antigen with attach in the following order: antibody on magnetic microparticle-antigen-antibody-chemiluminescent label. The magnetic microparticle is then washed off. The amount of antibody-antigen-enzyme is measured by adding pre-trigger solution and trigger solution and measuring the light produced. This type of immunoassay produces light when combined with its substrate, i.e., a specific binding member. The chemiluminescent reaction offers high sensitivity and ease of measurement. This type of immunoassay involves a noncompetitive sandwich format that yields results that are directly proportional to the amount of analyte present in the sample. Another type of this assay involves a competitive format, wherein an antigen and a labeled antigen are competing for the same antibody site, or an antibody and a labeled antibody are competing for the same antigen site. For example, a magnetic microparticle is coated with an antibody for a specific antigen. In addition, a reagent, which is a labeled antigen, is added. The labeled antigen and the unlabeled antigen compete for antibody sites of the magnetic microparticle. Only when the labeled antigen attaches to the antibody on the microparticle can light be produced via the chemiluminescent reaction. The amount of antigen in the original sample is indirectly proportional to the quantity of light produced. As used herein, the term "magnetic" means paramagnetic. The purpose of the pre-trigger solution is to enable the release of a chemiluminescent material, e.g., acridinium, from the conjugate that has bound to the magnetic microparticles in an immunoassay. In addition, the pre-trigger solution adds hydrogen peroxide and lowers the pH to a level so that no photons are emitted from the chemiluminescent material. A trigger solution complementary to the pre-trigger solution raises the pH back to neutral by means of a basic solution, e.g., sodium hydroxide solution, and allows the hydrogen peroxide to generate photons from the chemiluminescent material.

As used herein the term "contaminant" means an agent that renders a substance impure, whereby the impure nature of the substance adversely affects the functional characteristics of the substance. As used herein, the terms "epoxy", "epoxy resin", and the like, mean one of various, usually thermosetting resins, capable of forming tight cross-linked polymer structures marked by toughness, strong adhesion, and high corrosion and chemical resistance, used especially in adhesives and surface coatings.

As used herein, the expression "barbed fitting" means a fluid power fitting used with a hose. A barbed fitting is characterized by the presence of angled barbs that grab and hold on the interior surface of a hose. A barb is an angled cylindrical feature on the exterior of a fitting that grabs and holds the interior surface of a hose. Barbs are designed so that the hose is easily mounted over the fitting, but is difficult to remove. As used herein, the expression "hose fitting" means a type of fitting used to connect a hose to another fluid component. As used herein, the expression "quick disconnect fitting" means a fitting designed for use with components that are moved often and for avoiding disrupting air pressure of the system or compromising safety.

As used herein, the term "vent" means an opening for the passage of a liquid, gas, or vapor. The opening that constitutes the vent can be equipped with a fitting.

Automated clinical analyzers that are contemplated for use with the system for the treatment of contaminants described herein include automated diagnostic analyzers, such as, for example, ARCHITECT® automated immunoassay analyzers, as modified to utilize the system for the treatment of contaminants described herein. A representative example of such an automated immunoassay analyzer that can be modified to utilize the system for the treatment of contaminants described herein is the ARCHITECT® i2000 automated immunoassay analyzer. This automated immunoassay analyzer is described, for example, in U.S. Pat. Nos. 5,795,784 and 5,856,194, both of which are incorporated herein by reference. U.S. Patent Application Publication Number 2006/0263248 A1, incorporated herein by reference, describes another automated immunoassay analyzer that can be adapted to use the liquid waste management system described herein. The system described in U.S. Patent Application Publication Number 2003/0223472 A1, incorporated herein by reference, can also be adapted to use the system for the treatment of contaminants described herein. In addition, the probe washing apparatus described in U.S. Patent Application Publication Number 2005/0279387 A1, incorporated herein by reference, can be adapted to use the system for the treatment of contaminants described herein. Still further, some of the sub-systems described in U.S. patent application Ser. No. 11/644,086, filed Dec. 22, 2006, incorporated herein by reference, can be adapted to use the system for the treatment of contaminants described herein Displacement air is routed through a gas scrubber, thereby removing unwanted contaminants from the displacement air and preventing the contaminants from contaminating the bulk liquid utilized in the automated clinical analyzer. Scrubber systems are a diverse group of air pollution control devices that can be used to remove particulates and/or gases from industrial exhaust streams. Traditionally, the term "scrubber" has referred to pollution control devices that used liquid to scrub unwanted pollutants from a gas stream. Recently, the term is also used to describe systems that inject a dry reagent or slurry into a dirty exhaust stream to scrub out acid gases. Scrubbers are one of the primary devices that control gaseous emissions, especially acid gases. Dry sorbent injection involves the addition of an alkaline material (usually hydrated lime or soda ash) into a gas stream to react with the acid gases. The sorbent can be injected directly into several different locations. The acid gases react with alkaline sorbents to form solid salts, which are removed in the particulate control device. These simple systems can achieve only limited acid gas removal efficiencies. Higher collection efficiencies can be achieved by exposing more surface area of the alkaline material to the acid gas. One side effect of scrubbing is that the process only removes the unwanted substance from the exhaust gases into a solid waste or powder form. If there is no useful purpose for this solid waste, it must be either contained or buried to prevent environmental contamination.

In the case of the unwanted contaminant carbon dioxide, a carbon dioxide scrubber is a container filled with particles of alkaline material, such as for example, sodium hydroxide (NaOH). As used herein, alkaline material means material having pH value in excess of 7.0. These particles absorb the carbon dioxide as the displacement air passes through the medium. Many varieties of gas scrubbers and materials contained therein are available and can be replaced according to a routine maintenance schedule. The effectiveness of the scrubber is diminished as more of the particles of the accessible material undergo reaction with the contaminant. Replacement of the scrubber can be simplified and expedited by means of using standard barb fittings or hose fittings, or quick-disconnect fittings.

Figure 1:
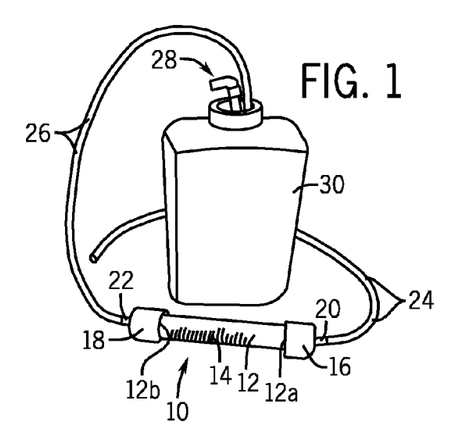
FIG. 1 is a perspective view that illustrates a gas scrubber and various connections associated with the gas scrubber.

Referring now to FIG. 1, a gas scrubber 10 comprised an elongated tube 12 having a sidewall 14 that encloses a bore (not shown). The bore contains a reagent that reacts with at least one contaminant in the atmosphere surrounding the automated clinical analyzer. When the contaminant is an acidic contaminant, e.g., carbon dioxide gas, the reagent is basic, i.e., having a pH value above 7.0. For example, if the contaminant is acidic, the bore can contain an alkaline material, e.g., sodium hydroxide. The tube 12 has a first end 12a covered by a first end cap 16 and a second end 12b covered by a second end cap 18. The sidewall 14, the first end cap 16, and the second end cap 18 are formed from material(s) that resist corrosion from moisture and from the alkaline material contained in the bore. Such materials include, but are not limited to, non-corrosive metals, such as, for example, stainless steel, and polymeric materials. The first end cap 16 can be joined to the elongated tube 12 by means of a friction fit, a snap fit, or a threaded fit. The second end cap 18 can be joined to the elongated tube 12 by means of a friction fit, a snap fit, or a threaded fit. A friction fit, a snap fit, and a threaded fit are well known to those of ordinary skill in the art. As shown in FIG. 1, a fitting 20 inserted into an opening (not shown) in the first end cap 16 enables the materials contained in the bore of the elongated tube 12 to communicate with the atmosphere surrounding the automated clinical analyzer. A fitting 22 into an opening (not shown) in the second end cap 18 enables the materials contained in the bore of the elongated tube 12 to communicate with the atmosphere surrounding the automated clinical analyzer. A fluid line 24 is connected to the fitting 20 at one end 24a of the fluid line 24. The other end 24b of the fluid line 24 communicates with the atmosphere surrounding the automated clinical analyzer. A fluid line 26 is connected to the fitting 22 at one end 26a of the fluid line 26 and the other end 26b of the fluid line 26 is connected to a straw assembly 28. The straw assembly 28 is fitted to a container 30, which contains the bulk liquid that is adversely affected by the contaminant in the atmosphere surrounding the automated clinical analyzer. The straw assembly 28 will be described in greater detail below.

Figure 2:
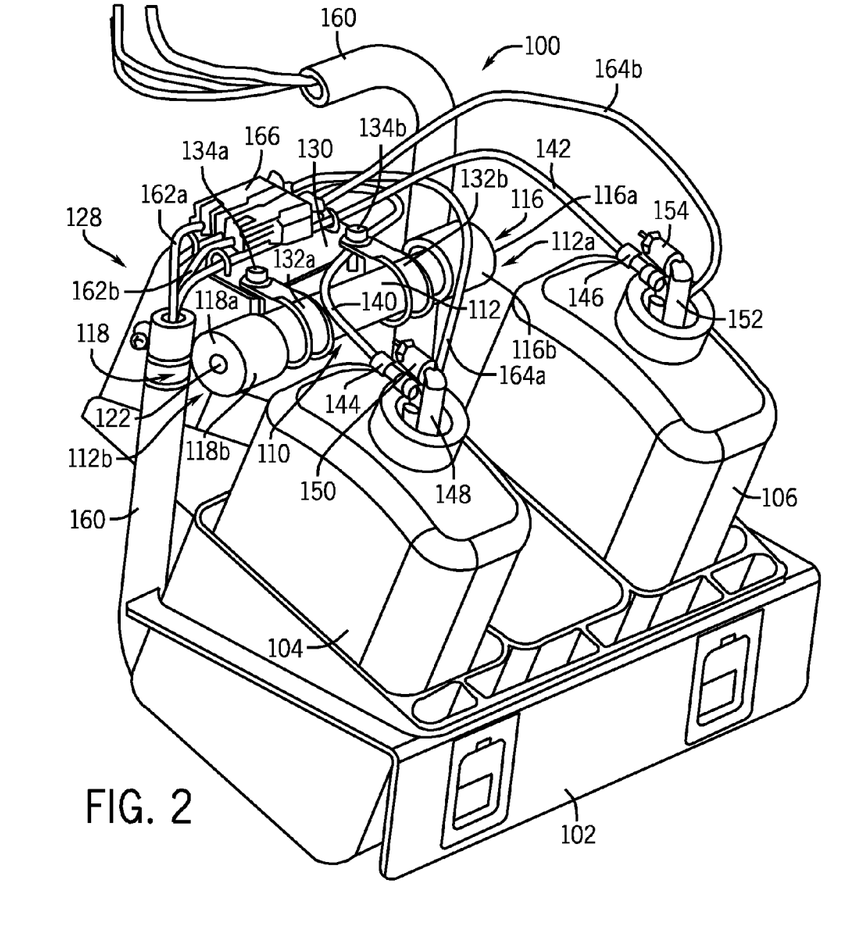
FIG. 2 is a perspective view that illustrates the various components of a gas scrubber and a straw assembly suitable for use in the invention described herein.

FIG. 2 shows how the gas scrubber described herein can be connected to a pick-up assembly. In FIG. 2, the pick-up assembly is designed such that all air leaks are eliminated, and all displacement air is forced to route through the gas scrubber. To maximize the effectiveness of the gas scrubber, the pick-up device in the container, sometimes called a straw assembly, should be designed in such a manner that all air leaks are eliminated, and all displacement air is forced to travel through the gas scrubber.

Referring now to FIG. 2, a pick-up assembly 100 comprises a tray or drawer 102 for supporting a container 104, e.g., a large bottle, for trigger solution and a container 106, e.g., a large bottle, for pre-trigger solution. A gas scrubber 110 comprises an elongated cylindrical container 112 having a sidewall 114. A first end 112a of the elongated cylindrical container 112 has an opening covered by a first end cap 116, and a second end 112b of the elongated cylindrical container 112 has an opening covered by a second end cap 118.

The sidewall 114 of the elongated cylindrical container 112 encloses a bore (not shown). The bore contains a reagent that reacts with at least one contaminant in the atmosphere surrounding the automated clinical analyzer. When the contaminant is an acidic contaminant, e.g., carbon dioxide gas, the reagent is basic, i.e., having a pH value above 7.0. For example, if the contaminant is acidic, the bore can contain an alkaline material, e.g., sodium hydroxide. The elongated cylindrical container 112, the first end cap 116, and the second end cap 118 are formed from material(s) that resist corrosion from moisture and from the alkaline material contained in the bore. Such materials include, but are not limited to, non-corrosive metals, such as, for example, stainless steel, and polymeric materials. The first end cap 116 can be joined to the elongated cylindrical container 112 by means of a friction fit, a snap fit, or a threaded fit. The second end cap 118 can be joined to the elongated tube 112 by means of a friction fit, a snap fit, or a threaded fit. A friction fit, a snap fit, and a threaded fit are well known to those of ordinary skill in the art.

The first end cap 116 has a top wall 116a and a skirt 116b depending from the top wall 116a. The second end cap 118 has a top wall 118a and a skirt 118b depending from the top wall 118a. The first end cap 116 has an aperture (not shown) formed through the top wall 116a. The second end cap 118 has an aperture (not shown) formed through the top wall 118a. Inserted in the top wall 116a of the first end cap 116 is a first fitting (not shown), which enables the bore to communicate with the atmosphere surrounding the automated clinical analyzer. Inserted in the top wall 118a of the second end cap 118 is a second fitting 122, which enables the bore to communicate with the atmosphere surrounding the automated clinical analyzer. The first fitting (not shown) can be connected to a fluid line (not shown), which in turn can be connected to a check valve (not shown). In an alternative embodiment, the first fitting (not shown) and the fluid line (not shown) connected to the first fitting can be eliminated, and the check valve (not shown) can be integrated with the first end cap 116. This alternative would result in a cost reduction by eliminating one fitting and one fluid line. Integration of the first end cap 116 with the check valve can be carried out by one of ordinary skill in the art. However, it would be preferred that a custom-made end cap containing a check valve be designed for use with the gas scrubber 110 described herein. The second fitting 122 is connected to a fluid line (not shown), which in turn is connected to a straw assembly, which is described below. This fluid line is not shown in FIG. 2 so that the second fitting 122 and the straw assembly can be viewed without obstruction. Fittings that can be used for the first fitting (not shown) include, but are not limited to, barbed fittings. Fittings that can be used for the second fitting 122 include but are not limited to, barbed fittings. The dimensions of the gas scrubber 110, i.e., length, volume, are variable, and they are selected on the basis of the expected life of the gas scrubber 108. A gas scrubber 110 expected to have a useful life of 10 years can have the dimensions of approximately six (6) inches in length and approximately 1.25 inches in outside diameter, and less than 1.25 inches inside diameter, i.e., diameter of the bore.

The tray or drawer 102 has an arm-like component 128 projecting therefrom. The arm-like component 128 has a platform 130 projecting therefrom. A pair of support rings 132a and 132b, which encircle the elongated cylindrical container 112, maintain the gas scrubber 110 in a fixed position, relative to the containers 104 and 106. Support rings are also often referred to as collar grips. The support rings 132a and 132b are attached to the platform 130 by means of bolts 134a and 134b, respectively, which pass through flanges of the support rings 132a and 132b, respectively. Other techniques of securing the gas scrubber 110 to the automated clinical analyzer can be used in place of the aforementioned bolts and support rings.

A fluid line 140 enables the trigger solution to be delivered to the fluid dispensing portion of the automated clinical analyzer. A fluid line 142 enables the pre-trigger solution to be delivered to the fluid dispensing portion of the automated clinical analyzer. A Luer lock 144 is used to connect the fluid line 140 to the straw assembly of the container 104. A Luer lock 146 is used to connect the fluid line 142 to the straw assembly of the container 106. A vent 148 enables displacement air to enter the container 104 containing the trigger solution. The end of the fluid line (not shown) that is not connected to the second fitting 122 of the gas scrubber 110 is connected to a barbed fitting 150 that communicates with the vent 148. A vent 152 enables displacement air to enter the container 104 containing the pre-trigger solution. A barbed fitting 154 is connected to the fluid line, if any, that is connected to the barbed fitting 154 that communicates with the vent 152. The addition of a check valve, such as a duck-bill valve or a diaphragm valve, mentioned previously but not shown in FIG. 2, positioned in either a fluid line (not shown) connected to the first fitting (not shown) on the first end cap 116 of the gas scrubber 110, or integrated with the first end cap 116 of the gas scrubber 110, can be used to reduce the quantity of a gas from the atmosphere surrounding the automated clinical analyzer from entering the gas scrubber 110 and reacting with the reagent, e.g., particles of alkaline material, in the gas scrubber 110. Thus, only displacement air that is drawn into the system by means of liquid dispensing would be scrubbed for contaminants in the atmosphere surrounding the automated clinical analyzer, thereby increasing the useful life and effectiveness of the reagent contained in the bore of the gas scrubber 110.

A conduit 160 having a large diameter, relative to the diameter of the fluid lines, bundles fluid lines that lead from the Luer lock connectors 144 and 146 to pumps, which pumps are used for pumping bulk liquids to the sub-system(s) of the automated clinical analyzer that is (are) used for dispensing liquids needed for clinical assays, such as for example immunoassays. These pumps are shown schematically in FIG. 3 and are designated by means of the reference numerals 218 and 220 in that drawing. In addition, the conduit 160 further bundles electrical wires 162a and 162b for liquid level sensors 164a and 164b, respectively, for the containers 104 and 106, respectively. It should be noted that the portion of the conduit 160 behind the tray or drawer 102 is not visible in FIG. 2. A connector 166 is used to connect the liquid level sensors 164a and 164b to the electrical wires 162a and 162b, respectively, which connect a source of power to the liquid level sensors 164a and 164b, respectively. Liquid level sensors 164a and 164b suitable for use with the containers 104 and 106, respectively, include, but are not limited to, magnetically actuated float sensors and mechanically actuated float sensors. With magnetically actuated float sensors, switching occurs when a permanent magnet sealed inside a float rises or falls to the actuation level. With mechanically actuated float sensors, switching occurs as a result of the movement of a float against a miniature (micro) switch. In the embodiment shown in FIG. 2, the liquid level sensor operates by means of magnetic operation of a reed switch.

It is greatly preferred that the straw assembly, which comprises a cap having threads (not shown) along with the Luer lock connector 144 for the fluid line 140, the vent 148, the barbed fitting 150 for the fluid line (not shown) for the gas scrubber 110, and the liquid level sensor 164a, have as little leakage as possible so that the air can flow into the system at one location only, i.e., the inlet of the gas scrubber. In order to ensure that the straw assembly has as little leakage as possible, the components of the straw assembly are preferably sealed with a sealant, such as, for example, epoxy resin. The sealant, which can be in the form of a cap that can be applied to the neck of the container of trigger solution, can be prepared by a molding process, such as, for example, injection molding. In order to apply the straw assembly to a container of bulk liquid, the cap of the container (not shown) is removed, typically by unscrewing the cap from the container. The cap of the container has threads (not shown) that mate with threads (not shown) on the neck of the container. The straw assembly comprises a cap having threads. The cap of the straw assembly is applied to the neck of the container by screwing the cap of the straw assembly onto the threads of the neck of the container.

In operation, as trigger solution is drawn from the container 104 and delivered to a sub-system of the automated clinical analyzer for dispensing liquids, the trigger solution consumed is replaced by displacement air. The displacement air, the source of which is the atmosphere surrounding the system, enters the system via the duck-bill valve, then enters the gas scrubber, where the reagent in the gas scrubber reacts with the carbon dioxide gas in the air, thereby preventing most of the carbon dioxide gas from entering the bulk liquid in the container 104. Because the carbon dioxide gas does not enter the container, the carbon dioxide does not react with the trigger solution, with the result that the pH of the trigger solution remains stable, i.e., at a pH greater than 7.0, for a relatively long period of time, e.g., as much as four weeks or greater. Under current conditions, it is expected that the trigger solution will be discarded after approximately 10 days. Thus, it can be seen that the stability of the trigger solution can be extended to at least about four weeks and the effects of the atmosphere surrounding the automated clinical analyzer can be minimized.

Figure 3:
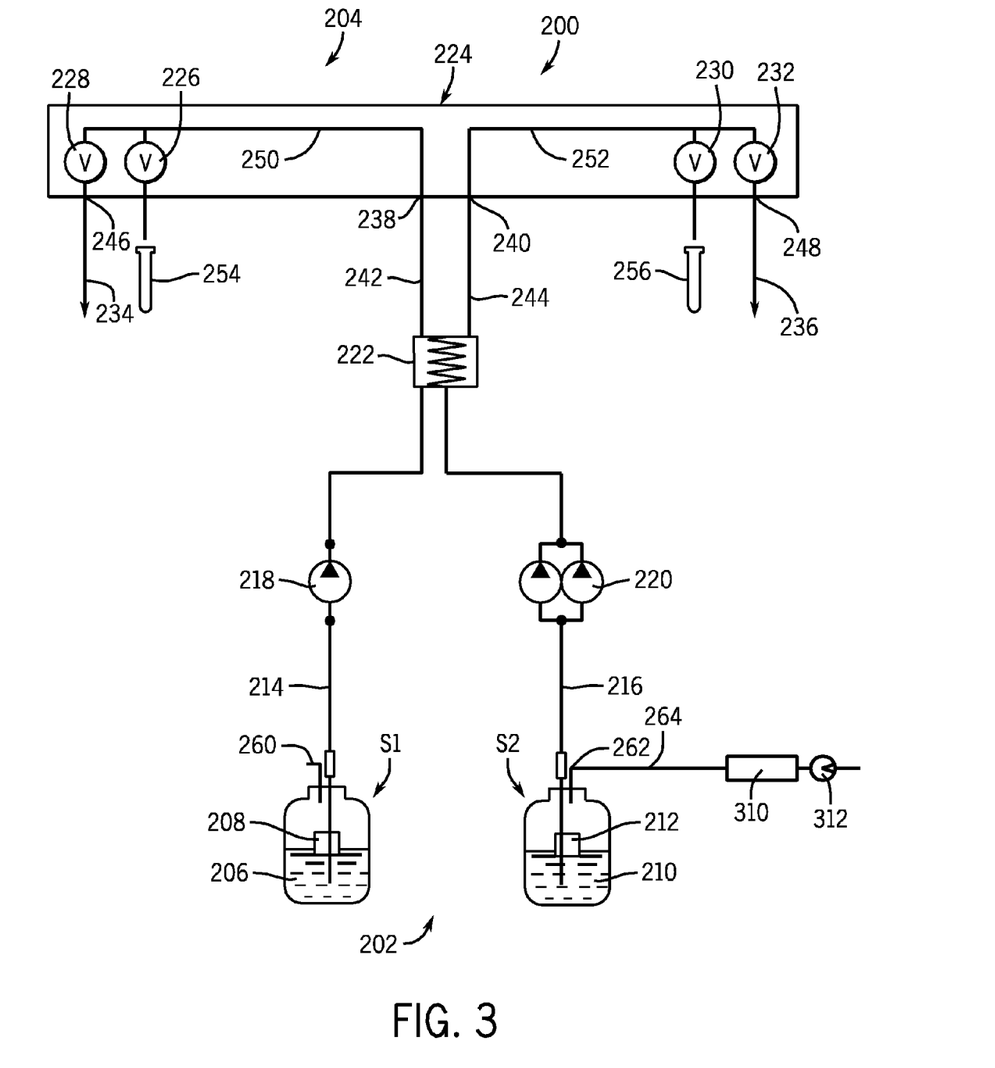
FIG. 3 is a schematic diagram that illustrates a system for dispensing pre-trigger solution and trigger solution for use in an automated diagnostic analyzer.

Referring now to FIG. 3, which is described in greater detail in U.S. patent application Ser. No. 11/644,086, filed Dec. 22, 2006, incorporated herein by reference, a sub-system 200 for dispensing a pre-trigger solution and a trigger solution comprises a storage area 202 for the pre-trigger solution and the trigger solution and a dispensing portion 204 for dispensing the pre-trigger solution and the trigger solution. The pre-trigger solution and the trigger solution are used to generate light from the contents of the reaction vessel at the end of the assay processing steps. The amount of light is measured and translated into values that have clinical significance. See, for example, U.S. Pat. Nos. 5,795,784 and 5,856,194, previously incorporated herein by reference, and U.S. Pat. No. 6,127,140, incorporated herein by reference, which further describes pre-trigger solutions and trigger solutions.

The storage area 202 comprises a container 206 for the pre-trigger solution, the container 206 being equipped with a sensor 208 for detecting the level of pre-trigger solution, and a container 210 for the trigger solution, the container 210 being equipped with a sensor 212 for detecting the level of trigger solution. A fluid line 214 connects the container 206 to the dispensing portion 204. A fluid line 216 connects the container 210 to the dispensing portion 204. The fluid line 214 comprises a pump 218 for the pre-trigger solution, and the fluid line 216 comprises a pump 220 for the trigger solution. A heater 222 for heating the pre-trigger solution and the trigger solution heats the pre-trigger solution in fluid line 214 and the trigger solution in fluid line 216. The pumps 218 and 220 can be positive displacement, valveless, rotary pumps. These pumps can be replaced by linear motion positive displacement pumps. Representative examples of pumps suitable for pumps 218 and 220 are commercially available from Fluid Metering Inc.

The dispensing portion 204 comprises a manifold 224 for the pre-trigger solution and the trigger solution. The manifold 224 has a dispense valve 226 for the pre-trigger solution and a bypass valve 228 for the pre-trigger solution. The manifold 224 further has a dispense valve 230 for the trigger solution and a bypass valve 232 for the trigger solution. The manifold itself is typically a machined part, typically made from polyvinyl chloride. The manifold 224 has entrance ports 238 and 240 for the fluid lines 242 and 244, respectively, that deliver the pre-trigger solution and the trigger solution, respectively, exit ports 246 and 248 for liquids that enter the fluid lines 234 and 236, respectively, fluid lines 250 and 252 for the pre-trigger solution and the trigger solution, respectively, mounting and locating features (not shown) for the solenoid valves. The manifold 224 further includes the dispensing tips (not shown) through which the pre-trigger solution and the trigger solution are delivered to the reaction vessels 254 and 256, respectively. The fluid from the bypass valve 228 for the pre-trigger solution and the fluid from the bypass valve for the trigger solution is routed through fluid lines 234 and 236, respectively, through an upper waste manifold into an accumulator, which are described in U.S. patent application Ser. No. 11/644,086, filed Dec. 22, 2006, previously incorporated herein by reference. The valves 226, 228, 230, and 232 are typically two-way solenoid valves.

Fluid lines mentioned herein, such as, for example, those represented by reference numerals 214, 216, 234, 236, 242, 244, 250, 252 are typically made of flexible silicone tubing. The diameter(s) of such tubing for a particular purpose is (are) readily determinable by one of ordinary skill in the art. A typical diameter for such tubing is approximately one-quarter inch.

The container 206 has a straw assembly S1, which includes the fluid line 214 and a vent 260. The container 210 has a straw assembly S2, which includes the fluid line 216 and a vent 262. A fluid line 264 connected to the vent 262 by means of an appropriate fitting contains the gas scrubber 310 and a check valve 312. The details of the gas scrubber 310 and the check valve 312 have been described previously by means of the description accompanying FIG. 2. The fluid line 264 is typically made of flexible silicone tubing. The diameter of such tubing for particular purpose described is readily determinable by one of ordinary skill in the art. A typical diameter for such tubing is approximately one-quarter inch.

When the trigger solution is withdrawn from the container 210 by means of the pump 220, the quantity of the trigger solution withdrawn is displaced by displacement air from the atmosphere surrounding the automated clinical analyzer. The displacement air from the atmosphere surrounding the automated analyzer enters the check valve 312 and then moves into the gas scrubber 310. The reagent in the gas scrubber 310 reacts with the contaminant, e.g., carbon dioxide, in the displacement air, thereby substantially removing the contaminant from the displacement air. The displacement air, with a greatly reduced quantity of contaminant, emerges from the gas scrubber 310 and enters the container 210 via the vent 262.

The gas scrubber described herein can be used with any liquid transfer system in which atmospheric air displaces the bulk liquid removed from a container, wherein the liquid is affected by specific gases in the atmosphere surrounding the automated clinical analyzer. For example, if the liquid is affected by oxygen gas ($O_2$), instead of carbon dioxide gas ($CO_2$), an oxygen gas ($O_2$) scrubber can be used. Representative examples of materials that can be used in a gas scrubber for oxygen gas ($O_2$) include, but are not limited to, copper, aluminum, and other metallic element that react readily with oxygen.

This invention enhances the stability of a bulk liquid so that the useful life can be extended, whereby the bulk liquid can be completely consumed prior to its expiration date. Such an extension eliminates waste, is friendly to the environment, and improves customer satisfaction.

The useful life of the scrubber is determined by the volume of air flowing through the scrubber, the concentration of the gas in the air, and how often a maintenance cycle would result in replacement of the scrubber. If the volume of a container of bulk liquid is 1 liter:

1. The concentration of carbon dioxide in the surrounding air is approximately 365 parts per million (ppm).
2. A cubic meter contains 1,000,000 cc of air or 40 moles of air, which contains 0.015 mole of carbon dioxide.
3. Each liter of air that passes through the scrubber contains 0.000015 mole of carbon dioxide.
4. The reaction of $CO_2$ and NaOH requires two molecules of NaOH to form $Na_2CO_3$ and $H_2O$, $3 \times 10^{-5}$ mole of NaOH are required for each liter of air that passes through the scrubber.
5. Because the molecular weight of NaOH is 40 g/mole, $1.2 \times 10^{-4}$ grams of NaOH per liter of air that passes through the scrubber.
6. If the analyzer consumes 12 liters/year and the scrubber is designed for a 10-year lifetime, $1.44 \times 10^{-2}$ grams of NaOH are required.
7. Estimating that the scrubber is 10% efficient, on account of not all of the NaOH is exposed to the stream of air, the scrubber would require 0.144 g of NaOH.

The quantities of NaOH or substitutes for NaOH, e.g., other alkaline materials that can react with carbon dioxide, can vary as a function of the desired useful life of the gas scrubber. A greater quantity of alkaline material provides a longer life to the gas scrubber.

The various components mentioned and described herein, such as, for example, containers, end caps, trays, fluid lines, conduits, connectors, electrical wires, fittings, valves, pumps, sensors, fastening components, reagents, automated clinical analyzers and the individual components thereof, are commercially available from numerous sources.

The following non-limiting example illustrates the feasibility of using a gas scrubber to inhibit the decrease of the pH of a bulk liquid.

EXAMPLE 1

The purpose of this example is to show that the gas scrubber described herein is viable for improving the stability of a bulk liquid used in an automated clinical analyzer.

Testing of the ARCHITECT® i2000 immunoassay analyzer showed that samples containing low levels of estradiol demonstrated a decrease in concentration values when tested over a time span within the expiration date of the trigger solution. Additional investigation indicated that absorption of carbon dioxide ($CO_2$) by the trigger solution was producing a downward shift in the pH value of the trigger solution, which, in turn, lowered the measured values of estradiol concentration in a biological sample. To counteract the absorption of carbon dioxide by the trigger solution, a gas scrubber was prepared by using a large medical syringe packed with sodium hydroxide (NaOH) crystals, and the gas scrubber was connected to a container of the trigger solution by means of a small capillary tube. In this example, an experimental carbon dioxide scrubber was tested using the ARCHITECT® i2000 immunoassay analyzer. However, the knowledge gained by this example can be applied to any ARCHITECT® immunoassay analyzer. In other words, this example indicates that the gas scrubber described herein can be connected to a container of the trigger solution suitable for use with any type of immunoassay analyzer that uses the type of trigger solution used in an ARCHITECT® immunoassay analyzer, and thereby reduce the effect of carbon dioxide on that trigger solution. This example further indicates that the gas scrubber described herein can be used to reduce the adverse effects resulting from contaminants from the atmosphere surrounding an automated clinical analyzer that enter any bulk liquid that is employed in the automated clinical analyzer.

The ARCHITECT® i2000 immunoassay analyzer was used for this testing. Five kits of reformulated reagent for an immunoassay for estradiol were run simultaneously. The packs of estradiol are described in detail in ARCHITECT® System ESTRADIOL package insert, Ref 7K72, B7K720, 77-3692/R2, incorporated herein by reference. Initially, five replicates per kit were programmed for testing, but the rate was changed to three replicates per kit after the fourth day of testing to conserve the reagents and the trigger solution. In order to accelerate the shift from a high pH level, i.e., greater than 7.0, to a low pH level, i.e., lower than 7.0, air was bubbled through two of the three containers of the trigger solution by means of a peristaltic pump at rate of 250 mL/min. Initially, the total time for bubbling time was 10 minutes, but that time was increased to one hour following the fourth day of testing.

The tubing for introducing a stream of air bubbles was placed directly into a container of the trigger solution, which was not equipped with the gas scrubber. For the container attached to the gas scrubber, the tubing for introducing the stream of air bubbles was routed through the gas scrubber before being directed into the container of the trigger solution, as shown in FIGS. _. The gas scrubber remained connected to the container of the trigger solution throughout the duration of the experiment. A third container of the trigger solution was not subjected to any stream of air bubbles, but was handled in the same manner as a conventional container of the trigger solution and served as the baseline, or control, condition. The fluidic system was flushed twice after each change of container, and the run was repeated with each of the three containers of the trigger solution each day. MCC low control was used as the sample throughout the experiment. The results are shown in FIGS. 4 and 5.

Figure 4:
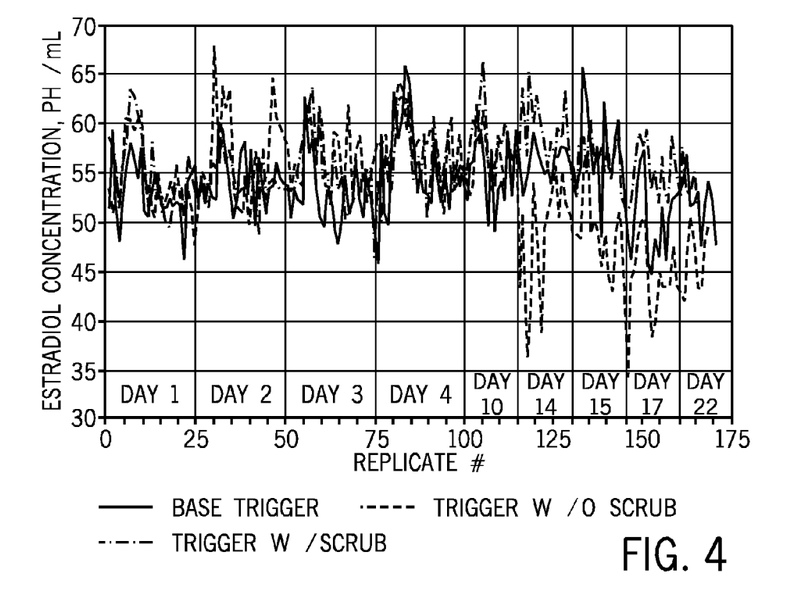
FIG. 4 is a graph illustrating the stability of a bulk trigger solution in an automated diagnostic analyzer under three conditions: (a) bulk trigger solution handled in a conventional manner without the gas scrubber and with no air bubbled through the trigger solution; (b) bulk trigger solution in which the system does not employ a gas scrubber and with air bubbled through the trigger solution; (c) bulk trigger solution in which the system employs a gas scrubber and with air bubbled through the gas scrubber into the trigger solution. The data in FIG. 4 was derived from a plot of each individual point.
Figure 5:
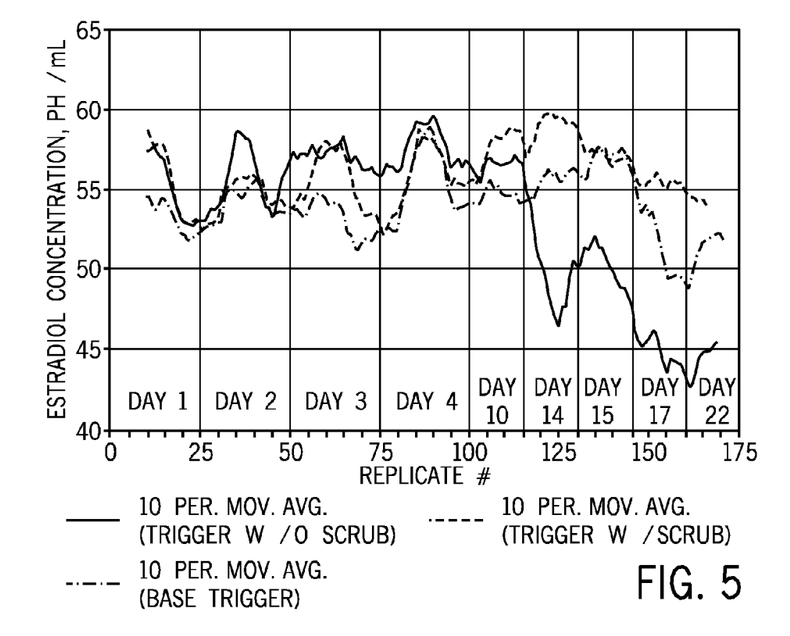
FIG. 5 is a graph illustrating the stability of a bulk trigger solution in an automated diagnostic analyzer under three conditions: (a) bulk trigger solution handled in a conventional manner without the gas scrubber and with no air bubbled through the trigger solution; (b) bulk trigger solution in which the system does not employ a gas scrubber and with air bubbled through the trigger solution; (c) bulk trigger solution in which the system employs a gas scrubber and with air bubbled through the gas scrubber into the trigger solution. The data in FIG. 5 was derived from a 10-point moving average of the individual data points shown in FIG. 4.

FIGS. 4 and 5 illustrate the trends of pH level of the trigger solution over the duration of the experiment, i.e., 22 days. In FIG. 4, each data point is plotted. In FIG. 5, a 10-point moving average of the same data shown in FIG. 4 is plotted. The data show that the gas ($CO_2$) scrubber has a substantial effect in maintaining the measured values of the concentration of estradiol over a lengthy period of time. Both the baseline container and the containers not equipped with a gas scrubber showed significant drifts in the values of the concentration of estradiol measured prior to the twentieth day of the experiment. It should be noted that the trigger solution is claimed to be stable for at least 20 days. Thus, it can be seen that the use of a gas scrubber, i.e., a carbon dioxide scrubber, significantly improves the stability of the trigger solution for an ARCHITECT® immunoassay analyzer.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An automated clinical analyzer comprising:
   a container to contain a bulk liquid including a material subject to deterioration as a result of reaction with a contaminant in a gas present in an atmosphere surrounding the container;
   a straw assembly coupled to the container;
   a gas scrubber having an inlet and an outlet;
   a fluid line to couple the outlet of the gas scrubber with the container via the straw assembly; and
   a lock disposed between the fluid line and the straw assembly.

2. The automated clinical analyzer of claim 1, wherein said gas scrubber comprises a chamber positioned between the container and the atmosphere.

3. The automated clinical analyzer of claim 1, wherein the container comprises a vent and the fluid line is to couple the gas scrubber to the vent.

4. The automated clinical analyzer of claim 1, wherein a check valve is positioned upstream of the inlet of the gas scrubber.

5. The automated clinical analyzer of claim 1 further comprising a reagent contained in the gas scrubber, the reagent to react with the contaminant to limit a change in a pH value of the bulk liquid.

6. The automated clinical analyzer of claim 5, wherein the reagent is an alkaline material.

7. The automated clinical analyzer of claim 6, wherein the alkaline material is sodium hydroxide.

8. The automated clinical analyzer of claim 1, wherein the automated clinical analyzer is an automated diagnostic analyzer.

9. The automated clinical analyzer of claim 8, wherein the automated diagnostic analyzer in an automated immunoassay analyzer.

10. The automated clinical analyzer of claim 1, wherein the lock is a Luer lock.

11. The automated clinical analyzer of claim 1 further comprising a tray to support the container and to hold a second container.

12. The automated clinical analyzer of claim 11 wherein the tray includes an arm and a platform coupled to the arm.

13. The automated clinical analyzer of claim 12 wherein the gas scrubber is coupled to the platform.

14. The automated clinical analyzer of claim 12 further comprising one or more liquid level sensors coupled to the platform.

15. The automated clinical analyzer of claim 14, wherein the liquid level sensor is a magnetically actuated float sensor.

16. The automated clinical analyzer of claim 11 wherein the one of the containers is to hold trigger solution and the other of the containers if to hold pre-trigger solution.

17. The automated clinical analyzer of claim 3 further comprising a barbed fitting communicatively coupled to the vent to control displacement air.

18. The automated clinical analyzer of claim 4, wherein the check valve is a duck-bill valve.

19. The automated clinical analyzer of claim 1 wherein the gas scrubber comprises a cylindrical tube.

20. The automated clinical analyzer of claim 1 further comprising a second fluid line to couple the inlet of the gas scrubber directly to the atmosphere.

* * * * *